United States Patent
Hutson et al.

(10) Patent No.: US 8,074,661 B2
(45) Date of Patent: Dec. 13, 2011

(54) METHOD AND APPARATUS FOR LASER TISSUE ABLATION

(75) Inventors: Michael Shane Hutson, Durham, NC (US); Glenn S. Edwards, Chapel Hill, NC (US)

(73) Assignee: Duke University, Durham, NC (US)

( * ) Notice: Subject to any disclaimer, the term of this patent is extended or adjusted under 35 U.S.C. 154(b) by 1289 days.

(21) Appl. No.: 10/516,163

(22) PCT Filed: Apr. 29, 2003

(86) PCT No.: PCT/US03/13227
§ 371 (c)(1),
(2), (4) Date: Apr. 21, 2005

(87) PCT Pub. No.: WO03/101529
PCT Pub. Date: Dec. 11, 2003

(65) Prior Publication Data
US 2005/0224460 A1 Oct. 13, 2005

Related U.S. Application Data

(60) Provisional application No. 60/384,877, filed on May 31, 2002.

(51) Int. Cl.
*A61B 19/00* (2006.01)
(52) U.S. Cl. .......................... 128/898; 606/3
(58) Field of Classification Search ............. 606/3–18; 607/88–95; 128/898
See application file for complete search history.

(56) References Cited

U.S. PATENT DOCUMENTS

| 5,403,306 | A | 4/1995 | Edwards et al. |
| 5,423,803 | A | 6/1995 | Tankovich et al. |
| 5,795,351 | A | 8/1998 | Clapham |
| 6,086,580 | A | 7/2000 | Mordon et al. |
| 6,090,100 | A | 7/2000 | Hohla |
| 6,358,243 | B1 | 3/2002 | Esterowitz et al. |
| 6,387,088 | B1 * | 5/2002 | Shattuck et al. .................. 606/2 |
| 6,482,199 | B1 * | 11/2002 | Neev .................................. 606/2 |
| 7,060,061 | B2 * | 6/2006 | Altshuler et al. ................. 606/3 |

FOREIGN PATENT DOCUMENTS
WO  WO 03/101529  12/2003

OTHER PUBLICATIONS

International Search Report and Notification of Transmittal dated Feb. 3, 2004.
Cole & McGahan, "Theory of Multilayers Heated by Laser Absorption," (1993) *J. Heat Transfer* 115: 767.
Crook, "The Reflection and Transmission of Light by Any System of Parallel Isotropic Films," (1948) *J. Opt. Soc. Am.* 38: 954.
Edwards et al., "Tissue Ablation by a Free-Electron Laser tuned to the Amide II Band," *Nature* vol. 371: 416 (Sep. 29, 1994).
Edwards Glenn, "Biomedical and Potential Clinical Applications for Pulsed Lasers Operating Near 6.45 μm," *Opt. Eng.* vol. 34, No. 5: 1524 (May 1995).

(Continued)

*Primary Examiner* — Ahmed Farah
(74) *Attorney, Agent, or Firm* — Jenkins, Wilson, Taylor & Hunt, P.A.

(57) ABSTRACT

A method and apparatus for ablating material. The material is preferably a heterogenous or composite material, such as animal tissue. A table top laser system can be employed in the invention. Alternatively, a larger laser, such as a free electron laser can be employed.

10 Claims, 8 Drawing Sheets

OTHER PUBLICATIONS

Edwards et al., "Comparison of OPA and Mark-III FEL for Tissue Ablation at 6.45 Microns," (2002) *SPIE* vol. 4633: 194.

Hector et al., "Hyperbolic Heat Conduction Due to a Mode Locked Laser Pulse Train," (1992) *Int. J. Eng. Sci.* 30: 1731.

Hutson et al., "Thermal Diffusion and Chemical Kinetics in Laminar Biomaterial Due to Heating by a Mark-III Free-Electron Laser," *Free Electron Laser Laboratory and Department of Physics, Duke University*, Feb. 7, 2002.

Joos et al., "Optic Nerve Sheath Fenestration With a Novel Wavelength Produced by the Free Electron Laser (FEL)," *Lasers Surg. Med.* (2000) 27: 191.

Lim & Shamos, "Evaluation of Kinetic Parameters of Thermal Decomposition of Native Collagen by Thermogravimetric Analysis," (1974) *Biopolymers* 13: 1791.

Madey, "Stimulated Emission of Bremsstrahlung in a Periodic Magnetic Field," (1971) *J. Appl. Phys.* 42: 1906.

Spörl et al., "Thermomechanical Behavior of the Cornea," (1997) *Ger. J. Opthamol.* 5: 322.

Tribble et al., "Dynamics of Gelatin Ablation Due to Free-Electron-Laser Irradiation," "Dynamics of Gelatin Ablation Due to Free-Electron-Laser Irradiation," *Phys. Rev. E* vol. 55, No. 6: 7385 (Jun. 1997).

Venugopalan & Mikić, "Thermodynamic Response of Soft Biological Tissues to Pulsed Infrared-Laser Irradiation," (1996) *Biophys. J.* 70: 2981.

International Search Report for PCT/US03/13227 dated Feb. 3, 2004.

Copeland et al., "First Human Surgery with a Free-Electron Laser," Case Report, 2002.

Davson, *Physiology of the Eye*, (5th Ed.) Pergamon Press, 1990.

Frank-Kamanenetskii, *Diffusion and Heat Transfer in Chemical Kinetics* (2d Ed.), Plenum Press, New York-London, 1969.

Greenberg et al., *The Amide Linkage: Selected Structural Aspects in Chemistry, Biochemistry and Materials Science*, Wiley-Interscience, 2000.

Kampmeier et al., "Thermal and Biomechanical Parameters of Porcine Cornea," *Cornea* vol. 19, No. 3, pp. 355-363 (2000).

Landau et al., *Fluid Mechanics* (2d Ed.), Pergamon Press, vol. 6, 1987.

Shripov et al., *Thermophysical Properties of Liquids in the Metastable (Superheated) State* (Chapter 8: Explosive Boiling of Liquids), Gordon and Breach Science Publishers, 1988.

Stryer, Lubert—*Biochemistry* (4th Ed), Stanford University, W. H. Freeman and Company, New York, 1995.

* cited by examiner

METHOD AND APPARATUS FOR LASER TISSUE ABLATION

RELATED APPLICATIONS

This application claims the benefit of U.S. Provisional Patent Application Ser. No. 60/384,877, filed May 31, 2002, the disclosure of which is incorporated herein by reference in its entirety.

GRANT STATEMENT

This work was supported by AFOSR grant F49620-00-1-0370. Thus, the U.S. Government has certain rights in the invention.

TECHNICAL FIELD

The present invention relates generally to surgical methods and apparatuses employing lasers, and more particularly to surgical methods and apparatuses employing lasers, such as free electron lasers and table top lasers, for tissue ablation.

Abbreviations

| | |
|---|---|
| DFEL | Duke University Mark III Free Electron Laser |
| FEL | free electron laser |
| OPA | optical parametric oscillator/amplifier |

BACKGROUND ART

The ability to employ lasers in medical applications has existed for some time. Ultraviolet lasers can be employed to resurface a subject's cornea to enhance the subject's vision. Visible lasers can be employed to repair a subject's damaged retina. Indeed, vision enhancement in humans employing an ultraviolet excimer laser has become commonplace. Infrared lasers are more typically used in dermatology. Due to charring and other collateral damage effects, however, it has been difficult to employ some infrared lasers in surgical applications beyond those listed.

Infrared free electron lasers (FELs), on the other hand, can be employed in a variety of applications ranging from surgery on the optic nerve (Joos et al., *Lasers Surg. Med.* (2000) 27: 191) to tumor and tissue ablation, including FEL neurosurgery (Edwards et al., (1994) *Nature* 371: 416; Edwards, (1995) *Opt. Eng.* 34(5): 1524; Copeland et al., (2000) International Biomedical Symposium SPIE, San Jose, Calif.). See also, U.S. Pat. No. 5,403,306 to Edwards et al. A goal of laser ablation is to remove tissue by "cold" etching, a process in which the etch pattern is defined by the irradiating laser beam, leaving peripheral tissue free from collateral damage due to photothermal and photomechanical effects. Various features of an infrared FEL, such as wavelength and pulse structure of the FEL can be considered when an infrared FEL is employed in ablation.

Various prior art references disclose the use of lasers in surgery. For example, U.S. Pat. No. 5,423,803 to Tankovich et al. describes a process for removing a fraction of a superficial epidermal layer from human skin using a laser that emits in the infrared spectrum and has an emission time less than or equal to 50 ns. But in this application, before laser irradiation, a composition comprising chromophores is applied to the skin that is to be treated. By employing either ultrasound or a laser, these chromophores are inserted into the intracellular spaces of the tissue. This treated area of the skin is then irradiated by a laser beam having sufficient energy to ionize the chromophores (after optical breakdown).

Similarly, U.S. Pat. No. 6,086,580 to Mordon et al. discloses a laser treatment for the ablation of skin. The '580 patent also requires applying a composition to the surface to be ablated and is directed to the removal of warts, scars and other structures from the skin of a subject. The '580 patent notes that lasers that emit in the infrared spectrum can be employed in the method of the '580 patent, such as $CO_2$ (10.6 μm), Er:YAG (2.94 μm), Ho:YAG (2.12 μm) and Nd:YAG (1.06 μm) lasers as well as lasers that emit in the visible spectrum, such as pulsed dye lasers (585 nm), ruby lasers (694 nm) and doubled Nd:YAG lasers (532 nm), however all of these methods and laser systems rely on the use of inserted chromophores.

These prior art methods and apparatuses, however, suffer the noted drawbacks. Additionally, FELs suffer from an additional drawback in that they typically require much space and are not table top laser systems. That is, the noted applications cannot be performed without large immobile laser systems (see, e.g. U.S. Pat. No. 5,795,351 to Clapham) and long and complex beam transport systems. In one aspect of the present invention, however, it is disclosed that efficient tissue ablation is not dependent on pulse structure, as was previously though. This observation facilitates the use, not only of any FEL meeting a given set of pulse structure-independent criteria in tissue ablation, but also the use of table top laser systems for this purpose. An ablation method employing a table top system would greatly enhance research in the fields of laser optics and optical engineering. Additionally, such a system would facilitate research in the area of medical applications of lasers and would assist in making laser-based surgery a more viable option for medical practitioners, as well as reducing the considerations of a patient, such as the need to transport the patient to a facility adapted for performing laser surgery.

With the advance of research into the application of light energy in medical fields, such as physical abrasion in oncology, orthopedics and dentistry, and industrial fields, such as precision machine engineering, semiconductor manufacture, and the like, demand has evolved for compact high-output table top laser systems that are adapted to accomplish these goals. Accordingly, a need exists for a method and apparatus employing a table top laser adapted for ablating material. Preferably, such an apparatus and method minimizes collateral damage to material surrounding the ablation site. A need also exists for an understanding of pulse structure features and/or conditions under which laser ablation of a material, preferably tissue, can be performed by employing an infrared FEL laser system or other infrared laser technology. The present invention solves these and other problems.

DISCLOSURE OF THE INVENTION

A method and apparatus for ablating a material, especially tissue, is disclosed. In a preferred embodiment, the method comprises: (a) directing laser radiation at a target material to be ablated; (b) irradiating the target material with one or more pulses of laser radiation having a duration ranging from about 1 nanosecond to about 10 microseconds, an energy per pulse greater than about 45 microjoules, and an average power greater than about 100 mW. Preferably the average power is greater than about 1 W.

The pulses can comprise a substructure, which itself can comprise "micropulses" as short as a picosecond, as is the case for an infrared Mark-III FEL in which a nominal pulse is on the order of microseconds in duration. It is also preferable that the laser radiation is supplied by a table top laser system. Suitable table top laser systems include solid state and gas phase lasers. It is also preferable that the target material comprises a composite material and even more preferable that the composite material comprises tissue.

Some of the objects of the invention having been stated hereinabove, other objects will be evident as the description proceeds, when taken in connection with the accompanying drawings as best described hereinbelow.

DETAILED DESCRIPTION OF THE INVENTION

I. Definitions

Figure 1:
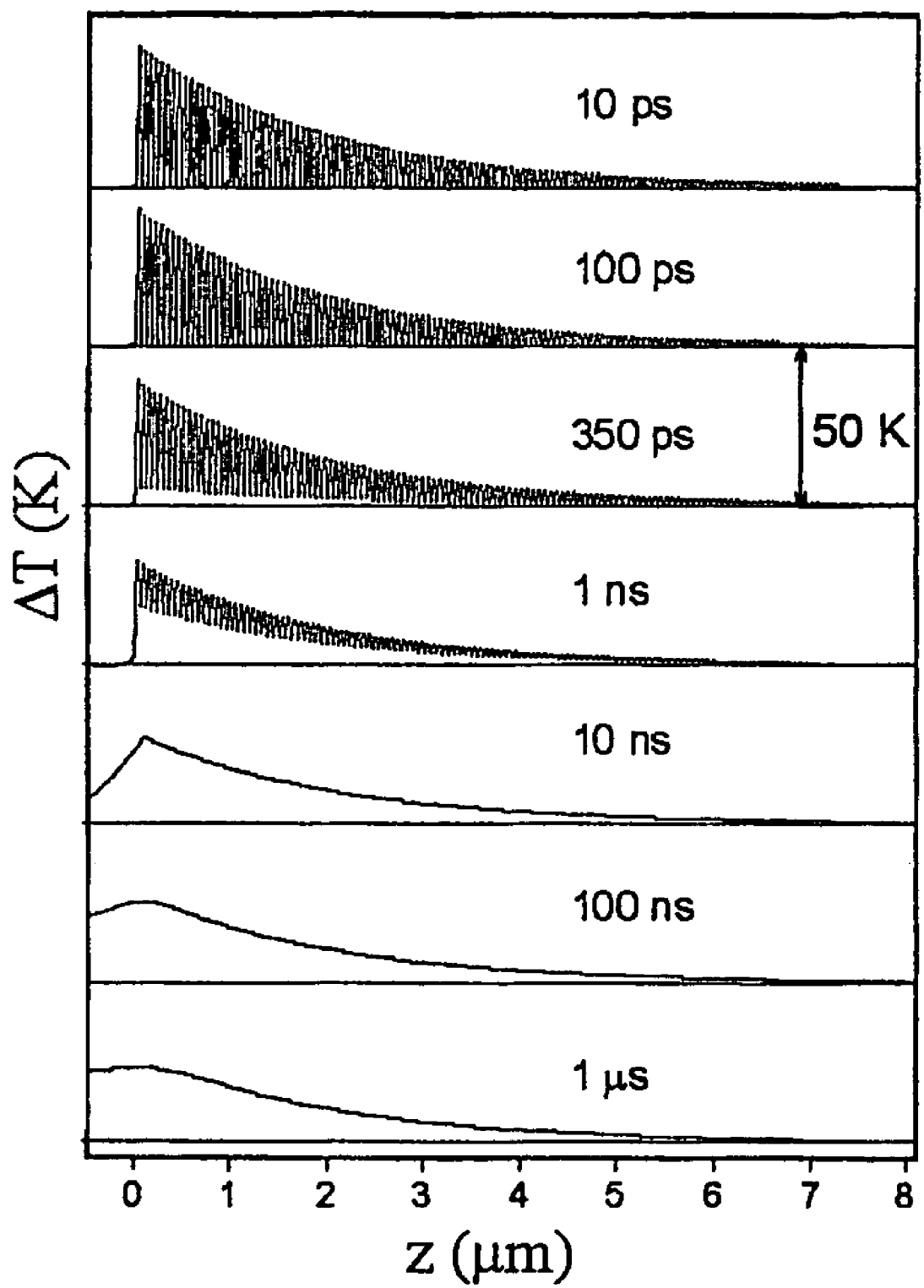
FIG. 1 is a plot depicting the thermal response to a single impulse at 3 µm; the absorption depth for protein is 8 µm, the absorption depth for saline is 12 µm (Edwards et al., (1994) Nature 371: 416), the refractive index for air is 1.00, the refractive index of cornea is 1.35, the density of protein is 1540 kg m$^{-3}$, the density of saline is 1000 kg m$^{-3}$, the density of air is 1.29 kg m$^{-3}$, the specific heat of protein is 1560 J kg$^{-1}$ K$^{-1}$, the specific heat of saline is 4184 J Kg$^{-1}$ K$^{-1}$, the specific heat of air is 1005 J Kg$^{-1}$ K$^{-1}$, the thermal conductivity of protein is 0.195 W m$^{-1}$ K$^{-1}$, the thermal conductivity of saline is 0.602 W m$^{-1}$ K$^{-1}$ and the thermal conductivity of air is 0.0292 W m$^{-1}$ K$^{-1}$.

Following long-standing patent law convention, the terms "a" and "an" mean "one or more" when used in this application, including the claims.

As used herein, the term "about," when referring to a value or to an amount of length, power, mass, weight, time, volume, concentration or percentage is meant to encompass variations of ±0% or ±10%, more preferably ±5%, even more preferably ±1%, and still more preferably ±0.1% from the specified amount.

As used herein, the terms "composite material" and "heterogenous material" are used interchangeably and mean a material that is not of uniform composition. One example of a composite material is tissue derived from an animal. Tissue comprises a wide range of materials, including proteins, nucleic acids, lipids, carbohydrates and other distinct materials, making it a heterogenous material. A composite material is not limited to tissue and can comprise any material comprising two or more components known or suspected to exist in a material. When ablation is performed on a composite or heterogenous material and the composite or heterogenous material is biological in origin (e.g. tissue), the composite or heterogenous material can be ablated in situ, in which case the material (e.g. tissue) is ablated while it is disposed in contact with another structure (e.g. the body of a subject), or ex situ, in which case the material (e.g. tissue) is not disposed in contact with another structure (e.g. removed from and not in the body of a subject).

As used herein, the term "homogeneous material" means a material that is of uniform composition. An example of a homogeneous material is a purified polymer.

As used herein, the term "tissue" means any structure derived from an organism. The term also encompasses any structure excised or removed from an organism. Thus, the present invention can be employed to ablate tissue in situ or ex situ. As used herein, an organism from which "tissue" is derived need not be exclusively a human being, but rather the term encompasses tissue derived from any organism. With respect to humans, the term includes a structure derived from either a living human or a cadaver. Preferably tissue is derived from a mammal, and more preferably from humans, rats, mice and sheep. The term "Tissue" encompasses any structure derived from any mammal or bird. More particularly, the structure can be derived from an animal selected from the group consisting of rodent, swine, bird, ruminant, and primate. Even more particularly, the animal can be selected from the group consisting of a mouse, a rat, a pig, a guinea pig, poultry, an emu, an ostrich, a goat, a cow, a sheep, and a rabbit. Most particularly, the animal can be a primate, such as an ape, a monkey, a lemur, a tarsier, a marmoset, or a human.

II. General Considerations

In one aspect of the present invention, material ablation applications are disclosed. In another aspect of the present invention, tissue ablation applications employing a table top laser system are disclosed. The following sections present a general discussion of some concepts relevant to the present invention.

II.A. Free Electron Lasers

The laser light emitted from an FEL is emitted from bunches of electrons traveling at very nearly the velocity of light. They are deflected by a series of magnetic poles. When the electrons are deflected, an electro-magnetic wave is radiated. The apparatus causing this deflection contains small magnets oriented somewhat like the teeth of two interlocking combs and consists of magnets with alternate north and south poles. This system is called an undulator, or in more vernacular terms a "wiggler" since it wiggles the electron bunches, which then emit light. If there is a light beam of an appropriate frequency in the vicinity of these electrons, the phenomenon of stimulated emission occurs. The electrons emit light in phase and at the same frequency as the initial light, creating a laser.

Stated another way, in a free-electron laser, a beam of relativistic electrons, that is, electrons that have been accelerated to speeds comparable with the speed of light, is passed through a transverse and periodic magnetic field. This results in periodic transverse movement of the electrons. Light is emitted in the direction of the electron beam as a result of the interaction between the electrons and the magnetic field, and is fed back through the wiggler by means of two opposed mirrors. Stimulated emission is generated by the interaction of the electromagnetic wave fed back and forth and the periodic magnetic structure.

II.B. The Duke University Mark III FEL

Experiments demonstrate that the Duke University Mark III Free Electron Laser (DFEL), an infrared FEL, is a particularly effective tool for etching soft biomaterials with little damage surrounding the site (Edwards et al., (1994) *Nature* 371: 416). Based on these observations, human neurosurgical (Copeland et al., (2000) *International Biomedical Symposium*, SPIE, San Jose, Calif.) and ophthalmic (Joos et al., (2000) *Lasers Surg. Med.* 27: 191) procedures were developed and have been performed successfully. With respect to the underlying physical mechanism, models based solely on average penetration-depth cannot adequately explain these results. A thermodynamic model has been proposed to account for a wavelength dependence observed in ablation procedures. This model suggests that the optical, thermal and mechanical properties of protein as distinct from saline are important (Edwards et al., (1994) *Nature* 371: 416). However, the dynamics of the model and how the model relates to the superpulse structure of the DFEL have not been well understood.

II.C. Tissue Ablation Processes Employing a Laser

The nature of the interactions between light emitted by a laser and biological tissue is complex and depends on multiple factors. The ablation of tissue achievable with an infrared FEL is due to heating both protein and water. Thus an exogenous chromophore is not required. When the structural integrity of the protein is compromised before the water superheats and vaporizes, tissue ablation is achieved. Non-FEL infrared lasers also are being used for tissue ablation at the present time, although application of these lasers typically results in collateral damage.

Ablation of the outer layers of the skin (possibly extending as far as the dermis) with the aid of a laser is carried out only with lasers emitting in the infrared spectrum. Therefore, such a laser preferably operates at a wavelength that is predominantly absorbed by water. However, the distribution of water in the skin and other tissues can depend on several factors, including the nature of the site in question, the type of skin or tissue being ablated and the age of the subject who is to be treated, when the ablation is performed in situ. Exemplary lasers that emit in the infrared spectrum and are typically employed to target intracellular water include $CO_2$ (operating at 10.6 μm), Er:YAG (operating at 2.94 μm) and Ho:YAG (operating at 2.12 μm) lasers. Laser surgery and tissue and tumor ablation, on the other hand, typically require a laser capable of operating at higher power levels in the infrared range, as discussed herein.

Lasers that emit in the visible spectrum or in the near infrared (wavelengths from about 400 nm to about 1000 nm), and have a large penetration depth in skin, are primarily employed for treating lesions of the pigment-based type and the vascular type. Exemplary lasers that emit in the visible spectrum include pulsed dye lasers (585 nm), which can be employed in the treatment of vascular lesions, and doubled Nd:YAG lasers (532 nm), which can be employed in the treatment of pigment-based lesions. Upon consideration of the present disclosure, those of ordinary skill in the art will recognize that these and other laser systems that have long been employed only in the treatment of surface lesions can be employed in the ablation of deeper tissues and even exposed tumor tissue.

The clinical and histological response of tissue to being irradiated with laser light varies considerably depending on the type of laser and the wavelength that is used. A number of effects can be generated in the target, and they directly depend on several factors, such as the energy per unit surface area (or flux) and on the power per unit surface area (or irradiance). By studying the interaction of radiation with biological tissues, it is possible to distinguish between a variety of mechanisms which occur. In the field of tissue ablation, the use of lasers is principally based on two types of mechanism, either the thermal effect, where the light energy is converted into heat energy, or the mechanical effect, where the light creates shockwaves.

The thermal effect results from the biological tissue absorbing the light energy associated with the laser beam and the local dissipation of this light energy in the form of heat energy. For a given wavelength, the degree to which the tissues are heated depends, in part, on the flux and the irradiance. Depending on the strength of the heating, effects such as coagulation, carbonization, explosive vaporization and ablation of the cells constituting the biological tissue can be observed.

When the heat energy is dissipated in the tissue, it can be preferable to match the laser irradiation period to a period referred to as the thermal relaxation time, in order to limit the thermal damage created in the adjacent tissues. From a physical point of view, this period of time is defined as the time the tissue requires to reduce its excess temperature by 1/e with respect to the initial temperature. If the duration of the laser irradiation is significantly less than this relaxation time, the heat will not be able to diffuse inside the tissue and will remain confined in the irradiated volume. Furthermore, if, within this time, the energy deposited in the target is sufficient to increase it to a temperature very much in excess of 100° C., this will cause superheating and local vaporization of the medium. The expansion of the vapor bubble inside the tissue, which has remained cool, generates thermoelastic waves of weak amplitude. This process of selective photothermolysis is, for example, used for treating angiodysplasias of the skin: the erythrocytes absorb the pulse, explode, are vaporized and the rapid expansion of this vapor causes the vessel to rupture, with extravasation of the blood.

Analysis of the absorption spectrum of the various tissues indicates that the optical penetration depth of the radiation depends on, among other factors, the wavelength of the laser. Thus, the dissipation of energy as heat takes place in an interactive volume which depends essentially on the penetration depth of the beam irradiated zone), the diffusion and thermal conductivity coefficients of the affected tissues, the local vascularization and ability of the target to maintain the heat stored or to lose it.

II.D. Table Top Laser Systems for Tissue Ablation

Since most medical applications of lasers require intense source levels, there are only a few types of lasers that can be employed in these fields. One type of laser that has been employed recently in the removal of a brain tumor in a human (CoDeland et al., (2000) *International Biomedical Symposium*, SPIE, San Jose, Calif.) and in corneal surgery (Joos et al., (2000) *Lasers Surg. Med.* 27: 191) is the FEL. Due to the wide tunability, pulse structure, and high average as well as peak powers achievable by the FEL, this type of laser is suited to medical applications. However, in order to operate, an FEL requires a source of relativistic electrons, a need that is commonly met by a linear accelerator, as well as a specialized array of precision mounted magnets, a specialized optical cavity, and high vacuum. Such FELs can cost a million dollars or more with a facility cost of millions of dollars as well. Thus, the tremendous costs associated with FELs can be a limiting factor in terms of the types of lasers that can be employed in laser-based medical applications.

Recent advances in the medical applications of lasers, notably in the fields of laser surgery and tissue ablation, have required infrared FELs as the laser source. While effective, an FEL can be expensive to build and operate and is immobile. A table-top laser system, on the other hand, limits the costs of installation and allows such lasers to be cited in closer proximity to the surgical suite. The requirements to construct new facilities for surgical use would entail modifications of a room nearby or possibly adjacent to the surgical suite. For a sufficiently compact laser system, a portable laser system can be transportable to the operating suite itself.

III. Applications of the Present Invention

In one embodiment, the present invention discloses a method of ablating material by employing a laser. In a preferred embodiment, the laser is a table top laser.

III.A. Method of Ablating Material

In one embodiment of the present invention a method of ablating material is disclosed. In a preferred embodiment, the method comprises (a) directing laser radiation at a target material to be ablated; (b) irradiating the target material with one or more pulses of laser radiation having a duration ranging from about 1 nanosecond to about 10 microseconds, an energy per pulse greater than about 45 microjoules, and an average power greater than about 100 mW.

In the first step of the preferred embodiment, the method comprises directing laser radiation at a target material to be ablated. The laser radiation can originate with a variety of lasers. For example, an FEL can be employed. In a more preferred embodiment, a table top laser system can be employed. Indeed, an advantage of the present invention over large, immobile and complicated laser systems is the ability to employ smaller table top laser systems. There is promising alternative infrared laser technology. Relaxing the constraints on the complex pulse structure of the infrared FEL indicates that either solid state or, more likely, gas phase lasers are potential table top technologies that can achieve infrared laser ablation of tissue.

When a non-table top laser system is employed, the directing of laser radiation can be achieved by relaying a laser output beam through a guide structure to a desired location, such as a surgical suite or other site where a material to be ablated is disposed. Such guide structures are known to those of skill in the art and are in place in many facilities, such as FEL laboratories. Additionally, many of these facilities are equipped with surgical suites and other environments adapted for tissue ablation operations.

A table-top laser system limits the costs of installation and allows such lasers to be cited in closer proximity to the surgical suite. The requirements to construct new facilities for surgical use would entail modifications of a room nearby or possibly adjacent to the surgical suite. For a sufficiently compact laser system, a portable laser system may be transportable to the operating suite itself.

A target material can comprise any material. Preferred target materials include composite materials. A preferred composite material is tissue. The tissue can be derived from any source (although animal tissue, and human tissue in particular) is preferred. The tissue can be disposed in situ (e.g. while situated in an animal), either the animal from which the tissue was derived, or from an animal acting as a host for the tissue, such as a subject that received the tissue in a transplant operation. The tissue can also be disposed ex situ (e.g. removed from an animal or culture), and can comprise a tissue culture.

A target material can also comprise a non-tissue material, such as bone, or a biological or non-biological material, such as a polymer. When a polymer is selected as a target material, the polymer can be homogeneous or heterogeneous. A polymer can be synthesized or can be isolated from a biological system.

Continuing with this embodiment of the present invention, in the second step of the preferred embodiment, the target material is then irradiated with one or more pulses of laser radiation having a duration ranging from about 1 nanosecond to about 10 microseconds, an energy per pulse greater than about 45 microjoules, and an average power greater than about 100 mW. Prefereably, the average power is preferably about 1 W. These pulses can have a substructure, with "micropulses" as short as a picosecond, as is the case for the infrared Mark-III FEL when the nominal pulse is microseconds in duration.

The present invention does not require the complex pulse structure of an infrared Mark-III FEL. Due to this relaxation of constraints on pulse structure, the present invention can be employed using a variety of table top lasers, larger lasers, or even infrared FELs with modified pulse structures. Moreover, this observation indicates that the only preferred properties of a laser system for ablating material are those identified above, namely wavelength, pulse duration, energy per pulse, average power, and pulse substructure, if any.

Additionally, as noted hereinabove, the present invention can be employed to ablate material from heterogenous and composite materials, as well as homogeneous materials. More particularly, the present invention can be employed to ablate composite and heterogenous materials, such as tissue. These materials have long been treated as homogeneous for ease of mathematical description.

Another advantage of the present invention is the ability to ablate material cleanly and without charring or any significant degree of collateral damage, including explosive vaporization effects. This ability is particularly desirable when tissue is ablated in situ. Further, the present invention can be employed to ablate various types of tissue, including tumor tissue, and is not limited to corneal tissue ablation.

IV. Preferred Laser Sources

While most types of lasers can be employed in the present invention, optical parametric oscillator/amplifier systems (OPAs) operating near 6.45 μm, a kHz repetition rate and having picosecond pulse lengths are not envisioned as compatible with this invention. See Edwards et al., (2002) *SPIE* 4633: 194. Lasers operating at any wavelength, for example 3.0 μm, 3.4 μm, 6.0 μm and 6.1 μm, can be employed in the methods of the present invention. Some of the many suitable laser systems are described hereinbelow.

IV.A. Free Electron Lasers

The observation that the ablation effect is not limited to the pulse structure of the Mark-III FEL is significant. Until the present invention, it was thought that the pulse structure of a laser system employed in tissue ablation was a critical factor in the efficiency of ablation. Previously, it was believed that the efficiency of ablation was a function of the pulse structure of the laser employed (Edwards, (1995) *Opt. Eng.* 34(5): 1524). With the disclosure of the present invention, however, this previously-held belief has been proven to be erroneous. As the specification and Laboratory Examples demonstrate, the present invention is not unique or limited to a given laser or type of laser. The present invention can be practiced with wide range of pulse structures operating at several different infrared wavelengths (for example 3.0 µm, 3.4 µm, 6.0 µm and 6.1 µm, as disclosed in the Figures), facilitating the use of potentially numerous technologies for infrared laser sources The associated Laboratory Examples demonstrate that any FEL or other infrared laser system can be employed as a source of laser radiation in the present invention. Moreover, it is not necessary to account for the idiosyncrasies that sometimes accompany each individual FEL. Thus, ablation of a material can be achieved using any FEL or other infrared laser system under the conditions disclosed herein.

IV.B. Table Top Laser Systems

In a preferred embodiment, a table top laser system can be employed as a source of laser radiation in the present invention. Table top laser systems that can be employed in the present invention can include either solid state or gas phase lasers.

A table top laser system offers many advantages over other laser systems for use in the present invention, as noted herein. For example, a table top laser system can be moved as required. This mobility facilitates the use of the present invention at a range of different environments (e.g. a surgical suite, a materials laboratory, etc.). The mobility of a table top laser system is in contrast to the large and immobile nature of a typical FEL system. Additionally, the ability to employ a table top laser system in the methods of the present invention offers an economic advantage. FEL systems and other large and immobile laser systems are costly to purchase and maintain. Table top laser systems, on the other hand, are less expensive to acquire and install and are less expensive to maintain. Moreover, table top laser systems can be self-contained and do not rely on any additional equipment in order to operate. Some lasers, such as FELs require associated equipment in order to operate. Table top systems generally require less equipment and at times no additional equipment, making them simpler, less expensive and easier to operate and maintain than larger laser systems.

As noted herein, commercially available table top lasers systems potentially offer the infrared wavelength, pulse duration, energy per pulse, average power, and pulse substructure, if any, preferred for ablating material when employing a method or apparatus of the present invention. Prior to the present invention, the potential for these laser systems and the modified pulse structures to meet the criteria to ablate tissue was not recognized. The present invention solves this and other problems.

Laboratory Examples

The following Laboratory Examples have been included to illustrate preferred modes of the invention. Certain aspects of the following Laboratory Examples are described in terms of techniques and procedures found or contemplated in accordance with this invention. These Laboratory Examples are exemplified through the use of standard laboratory practices. In light of the present invention and the general level of skill in the art, those of skill will appreciate that the following Laboratory Examples are intended to be exemplary only and that numerous changes, modifications and alterations can be employed without departing from the spirit and scope of the invention.

Laboratory Example 1

Theoretical Model

Cornea was modeled for two reasons. First, there is extensive experimental data to support the model (Davson, (1972) *The Physiology of the Eye*, Academic Press, New York; Kampmeier et al., (2000) *Cornea* 19: 355; Privalov & Tiktopulo, (1970) *Biopolymers* 9: 127; Lim & Shamos, (1974) *Biopolymers* 13: 1791; St er, (1995) *Biochemistry*, 4$^{th}$ ed., W.H. Freeman and Company, New York, p 32; Liebman et al., (2000) *The Amide Linkage*, John Wiley and Sons, New York, Chapter V; Spörl et al., (1997) *Ger. J. Opthamol.* 5: 322). Second, the regularity of its structure allows a relatively detailed theoretical treatment. Cornea predominantly comprises highly ordered, alternating sheets of the collagen (a protein) and water, each about 30 nm thick. Collagen molecules are assembled in cylindrical bundles, each 22-32 nm in diameter, which are aligned and close packed in the protein sheets.

The Duke Mark III FEL produces a superpulse, comprised of a 2-6 microsecond burst of picosecond pulses at a repetition rate of 2.85 GHz, typically repeated at 10-30 HZ (Madey, (1971) *J. Appi. Phys.* 42:1906). FEL experiments demonstrate the material removal begins on the 100 ns time scale (Tribble et al., (1997) *Phys. Rev. E* 55: 7385). Since thermal diffusion over a distance of 30 nm in an aqueous environment occurs with a relaxation time of about 850 ps (van Gemert & Welch, (1995) *Optical-Thermal Response of Laser-Irradiated Tissue*, Plenum Press, New York, Chapter XIII), that picosecond pulses can be idealized as impulses to a good approximation. On the other hand, the 350 ps pulse separation was considered explicitly.

Thermal diffusion typically is described with Fourier's equation, where last heating of the medium is accounted for by an additional source term 0, to yield the heat balance equation:

$$\rho c_p \frac{\partial T}{\partial t} = \kappa \nabla^2 T + Q \qquad (1)$$

where $\rho$ is the density $c_p$ is the specific heat at constant pressure, T is the temperature and $\kappa$ is the thermal conductivity (Landau & Lifshitz, (1987) *Fluid Mechanics*, 2$^{nd}$ ed., Pergamon Press, Oxford, Chapter V). The heat balance equation is applied to a laminar system representative of cornea. The specific geometry is a half-space of air (z<0), then 500 alternating layers of protein and saline (0<z<15 µm), each 30 nm thick, and then a semi-infinite saline substrate (z>15 µn). The protein has the optical and thermal properties of collagen, and both air and saline are characterized by distinctive optical and thermal properties (Edwards et al., (1994) *Nature* 371: 416; Kampmeier et al., (2000) *Cornea* 19: 355) of the multilayer thermal diffusion model (Cole & McGahan, (1993) *J. Heat Transfer* 115: 767). Each layer is assigned a local axisymmetric Green's function (GF). The local GFs are Hankel transformed to eliminate the Bessel functions, temporally truncated to avoid aliasing and the singularity at zero frequency, and Fourier transformed. The resulting functions are then convoluted with the axial pattern of heat deposition, where reflection and interference are treated exactly (Crook, (1948) *J. Opt. Soc. Am.* 38: 954); however, scattering of mid-infrared radiation is a small effect and is not included. The exposure geometry and radial thermal relaxation time yield analytical simplifications. Laser irradiation is normal to the surface at z equals zero with a Gaussian profile, i.e. the axisymmetric system reduces the analysis to two dimensions. In addition, as confirmed by a 2-D calculation, the radial thermal relaxation time for a 50 µm spot size is milliseconds (van Gemert & Welch, (1995) *Optical-Thermal Response of Laser-Irradiated Tissue*, Plenum Press, New York), where the interest is for time shorter than several hundred nanoseconds. Consequently, a one-dimensional calculation on the z-axis is a good approximation. Layer temperatures in Hankel-Fourier space were calculated with an axial spacing of 6 nm, multiplied by the Fourier transform of the FEL pulse structure, and fast Fourier transformed to yield the temperature rise $\Delta T(z,t)$. Programs to calculate temperature distributions were written in Array Basic (Thermo Galactic, Salem, N.H., United States of America) and executed in the GRAMS/32™ environment.

For completeness, two complications have been considered. It has been pointed out that the use of Fourier's equation fails to account for the finite speed of thermal wave propagation, which is accounted for by the hyperbolic heat conduction equation (Hector et al., (1992) *Int. J. Eng. Sci.* 30: 1731). The present comparison of the two approaches reveals small deviations limited to the first few picoseconds following an impulse. In addition, rapid heating by a picosecond FEL pulse results in transient pressure pulses, tens of MPa in magnitude, that decay within several picoseconds with a small volume expansion and an inconsequential amount of work.

Results and Discussion of Laboratory Example 1

A. Laser Heating and Thermal Diffusion

FEL wavelengths of interest include 3.0 µm, 3.4 µm, 6.0 µm and 6.1 µm. One µJ per impulse is delivered to a Gaussian spot of 50 µm ($e^{-2}$ radius) and the temperature is tracked on the symmetry axis. FIG. 1 summarizes the thermal response to a single impulse. Distinctive patterns in temperature are evident from 10 ps through 1 ns due to the differences in absorption for protein and water in this laminar system. Interlayer diffusion and an indication of a surface enhancement are evident on the nanosecond time scale. By 10 ns the temperature profiles are independent of laminar structure. Exponential decay in z due to Beer's law is evident at all times.

It is instructive to introduce some physical concepts to interpret this case before proceeding to consideration of a train of impulses. As shown in FIG. 1, remnants of the layer specific absorption patterns remain until several nanoseconds after the laser pulse. At 3 µm, the saline layers are relative heat sinks during that period. While the temperature of the air layer is always less than the surface layer, air is not effective as a heat sink due to its much lower thermal conductivity. The ratio of $\kappa_{saline}:\kappa_{protein}:\kappa_{air}$ is 21:7:1. FIG. 1 indicates that thermal relaxation is incomplete at 350 ps, i.e. when the next pulse arrives in a Mark III macropulse.

Figure 2:
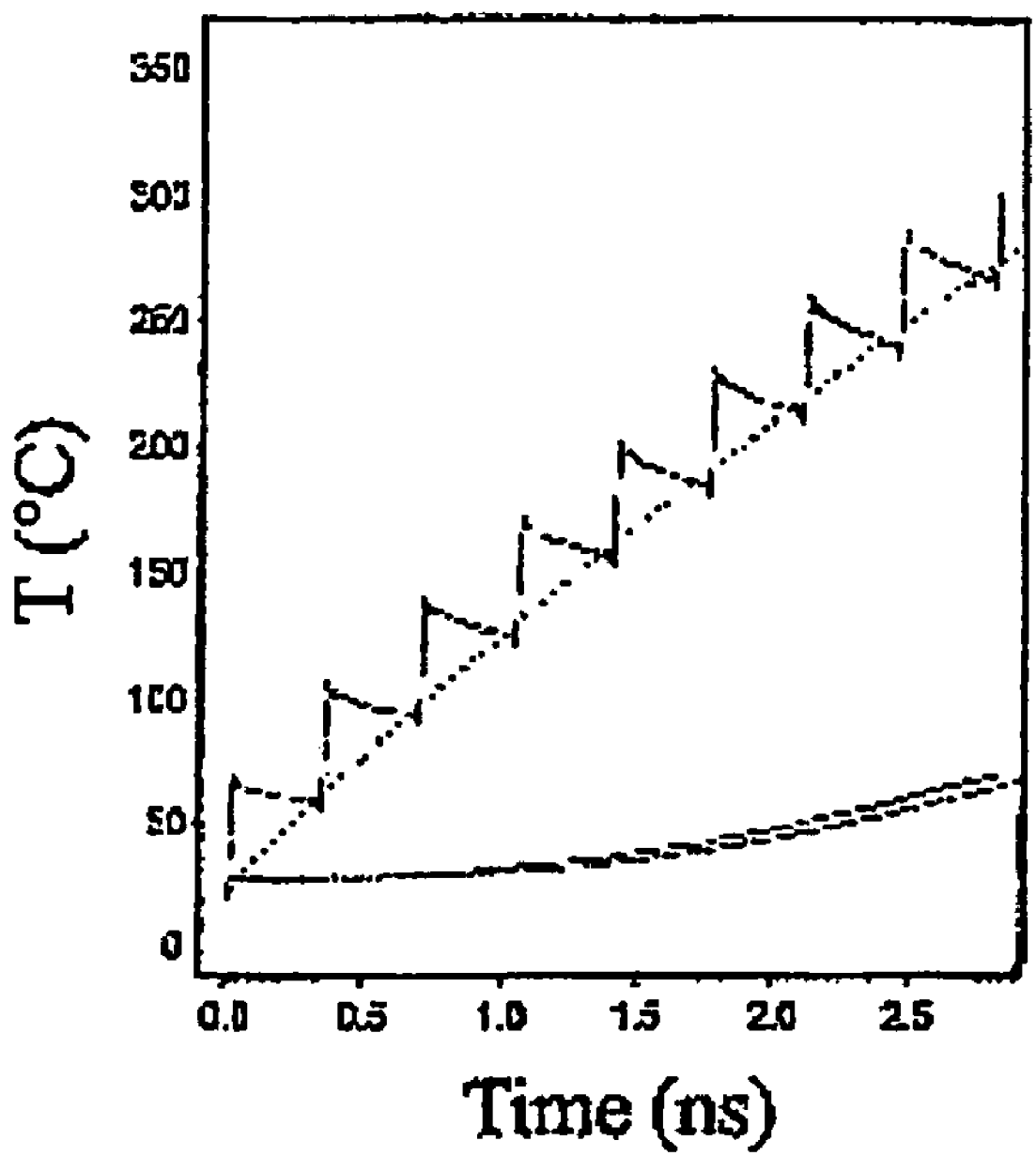
FIG. 2 is a plot depicting the thermal response of surface layers exposed to a train of impulses at 3 µm; in addition, the FEL superpulse structure, protein (solid) and water (dotted) is compared to a 16.2 ns pulse with the same average energy, protein (dashed) and water (dot-dash) and the initial temperature was 25° C.
Figure 2A:
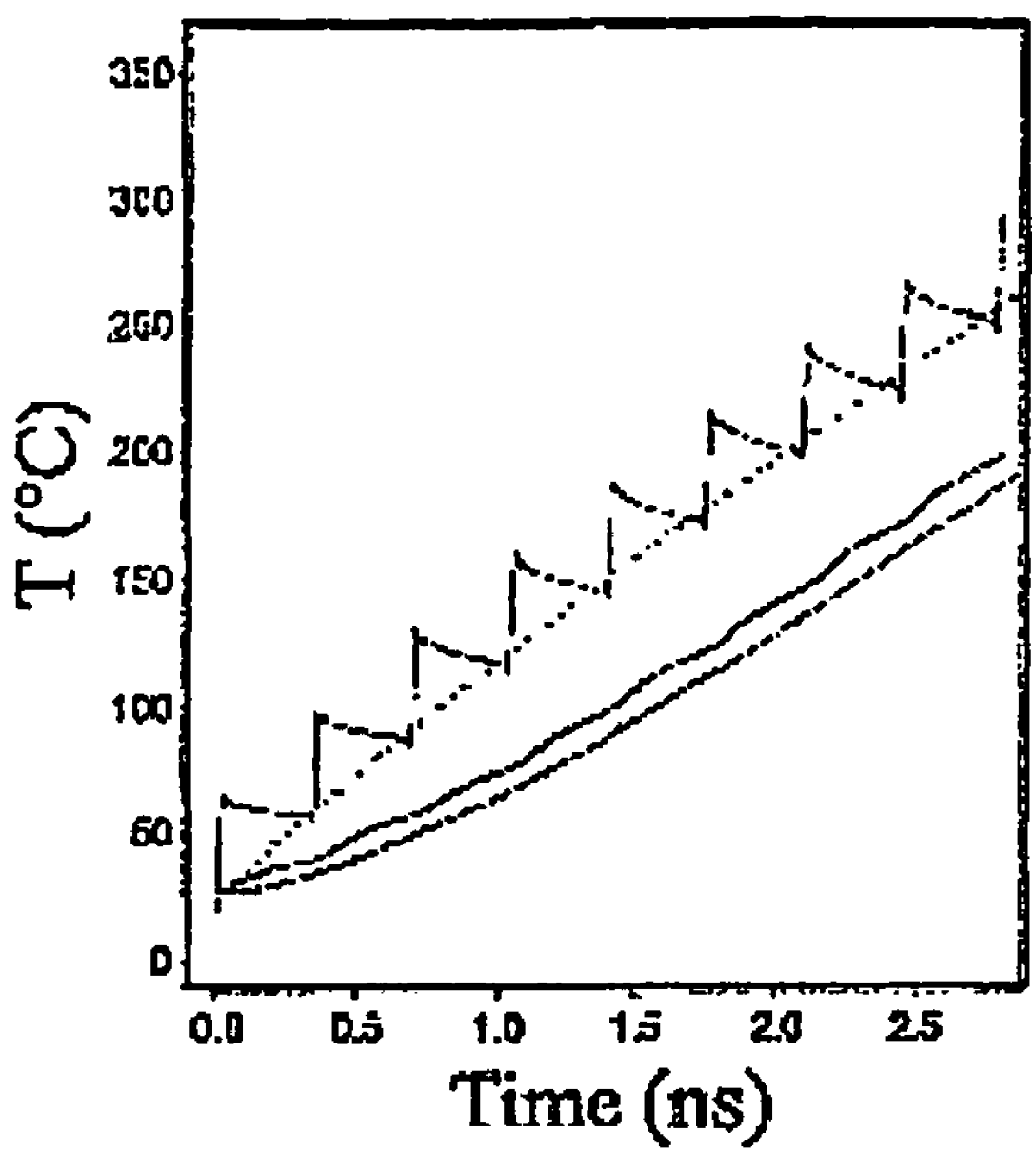
FIG. 2A is a plot depicting the thermal response of layers 200 nm below the surface exposed to a train of impulses at 3 µm; in addition, the FEL superpulse structure, protein (solid) and water (dotted) is compared to a 16.2 ns pulse with the same average energy, protein (dashed) and water (dot-dash) and the initial temperature was 25° C.

FIGS. 2 and 2A summarize the thermal response to a train of such impulses separated by 350 ps, demonstrating a relatively shallow "staircase" or "saw tooth" on a rising background temperature. Competition between the layer-specific rates of energy absorption, i.e. direct laser heating, and the rate of thermal diffusion results in temperature differences between adjacent saline and protein layers on the nanosecond timescale. At 3 µm, the laser energy is predominantly absorbed by the saline layers. The rate of direct laser heating outpaces the rate of diffusion losses in the saline layers and consequently the temperatures of the protein layers increasingly lag behind (FIGS. 2 and 2A).

The temperature difference in a neighboring pair of protein and saline layers is exaggerated at the surface (FIG. 2) when compared to 200 nm into the material (FIG. 2A). For this wavelength, the temperature of the outermost saline layer is comparable to the subsurface saline layer, which is defined as that layer 200 nm below the surface. However, the temperatures of the surface and subsurface protein layers differ significantly. At 3 µm (FIGS. 2 and 2A), the temperature of the surface protein layer lags behind the subsurface protein layer. The temperature of the surface protein layer (FIG. 2), which has only one neighboring heat source, rises more slowly than the subsurface protein layer (FIG. 2A), which is sandwiched between two heat sources.

Calculations in which the surface layer is saline instead of protein show comparable effects. At 3 µm, the temperature of the surface saline layer greatly exceeds the underlying saline layers because the surface layer is adjacent to only one protein heat sink. Thus, the enhancement in the surface temperature differences is due to two features. First it is a property of laminar materials where the layers have distinct absorption coefficients for the incident radiation. Second, the ambient air layer must be a relatively poor heat sink, i.e., the thermal conductivities of each laminar material must exceed that of air.

A comparison of FIGS. 1, 2 and 2A indicates that for these exposure conditions, a single impulse will not lead to vaporization. In contrast, a train of impulses with a repetition rate of 2.85 GHz does rapidly heat the saline layers to temperatures well in excess of 100° C. Such rapid laser heating superheats saline under these conditions (Skripov et al., (1988) *Thermophysical Properties of Liquids in the Metastable (Superheated) State*, Gordon and Breach Science Publishers, New York; Venugopalan & Mikić, (1996) *Biophys. J.* 70: 2981). More specifically, for a heterogenous nucleating density of $10^{15}$ m$^{-3}$ the exposure conditions at 3 µm satisfy the criterion for superheating by five and three orders of magnitude, respectively. Thus, the temperature of the saline layers increases until the onset of homogeneous nucleation of the vapor phase, i.e. explosive vaporization. The highest superheating temperature observed for an aqueous salt solution at 1 atm is 3020° C. (Skripov et al., (1988) *Thermophysical Properties of Liquids in the Metastable (Superheated) State*, Gordon and Breach Science Publishers, New York).

B. Chemical Kinetics

Figure 3:
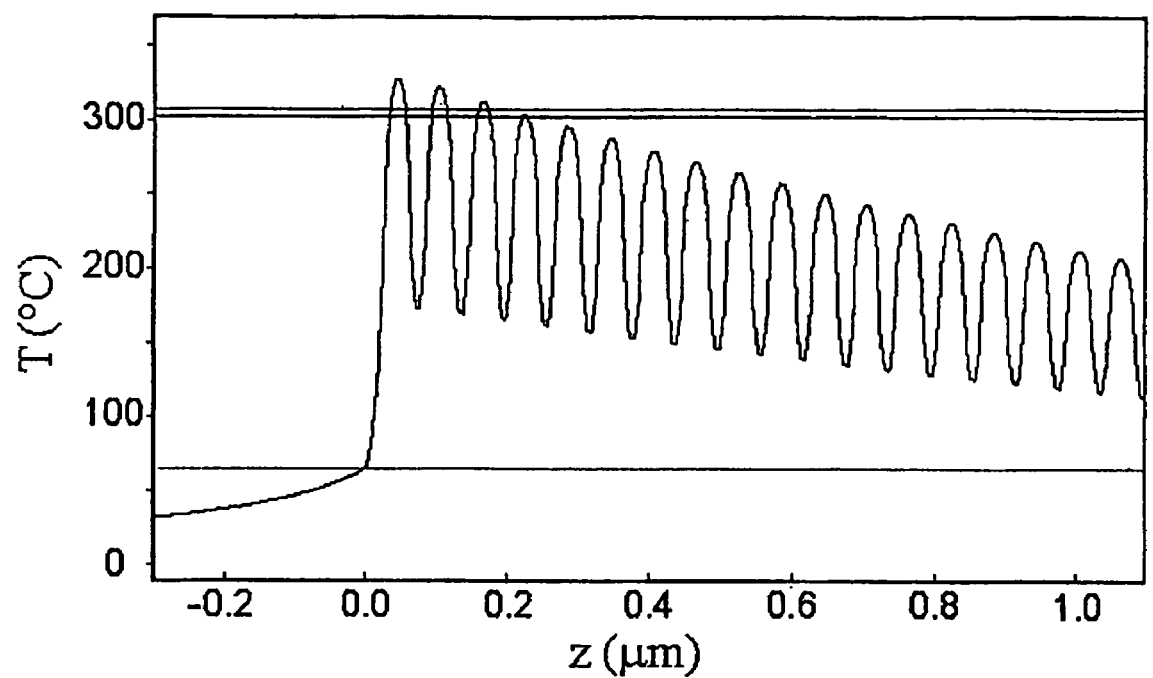
FIG. 3 is a plot depicting the thermal response to a train of impulses at 3 µm; the initial temperature was 25° C. and the horizontal lines mark three characteristic temperatures, namely 65° C., 302° C. and 307° C.

Thermal diffusion in this laminar system needs to be considered in light of several characteristic temperatures as shown in FIG. 3. First, we assume 302° C. is the superheat limit for saline. The temperature profile shown in FIG. 3 corresponds to the time at which the hottest saline layer first exceeds this limit. Second, collagen denaturation via the helix-coil transition is broad, with a peak temperature of 65° C. (Privalov & Tiktopulo, (1970) *Biopolymers* 9: 127). Third, thermogravimetric measurements demonstrate a broad feature with a slow heating (3° C./min) peak decomposition temperature of 307° C. (Lim & Shamos, (1974) *Biopolymers* 13: 1791). This thermal decomposition was found to be a second order reaction, attributed to breaking of the amide bond. In the following, the consequences of heating to the critical temperature on the 10 ns timescale are considered.

The kinetics of thermal decomposition can be treated with the Arrhenius model for a second order reaction, $$\frac{1}{C}\frac{dC}{dt} = A_2 C e^{-E/RT(t)} \quad (2)$$

where $A_2$ is the Arrhenius prefactor, R is the gas constant, E (82 kJ/mol) is the activation energy and C (3.14 mol L$^{-1}$) is the residue concentration for collagen (Stryer, (1995) *Biochemistry*, 4$^{th}$ Ed., W.H. Freeman and Company, New York, p. 32). A literature value for the prefactor was unavailable; however, analysis of the thermogravimetric data (Lim & Shamos, (1974) *Biopolymers* 13:1791) does yield a good approximation. More specifically, it was observed that the concentration of material can be reasonably approximated as inversely proportional to temperature for the decomposition process centered at 3070° C., yielding a prefactor of $3.0\times10^4$ L mol$^{-1}$ s$^{-1}$. This value is consistent with a peak decomposition temperature 307° C. at a heating rate of 3° C. per minute. However, the Arrhenius model indicates that essentially no thermal decomposition occurs on the 100 ns timescale for the temperatures indicated in FIG. 3.

Since hydrolysis of the amide bond is an exothermic process (Liebman et al., (2000) *The Amide Linkage*, John Wiley and Sons, New York, Chapter V), the possibility of spontaneous thermal explosion was also investigated, where the exponential temperature dependence of the exothermic reaction can overwhelm the linear temperature dependence of heat diffusion (Frank-Kamenetskii, (1969) *Diffusion and Heat Transfer in Chemical Kinetics*, 2$^{nd}$ ed., Plenum Press, New York, Chapters VI and VII). The criterion for spontaneous thermal explosion is expressed in terms of a dimensionless parameter. For the temperatures summarized in FIG. 3, this system fails to satisfy this criterion for spontaneous thermal explosion by twelve orders of magnitude.

Figure 4:
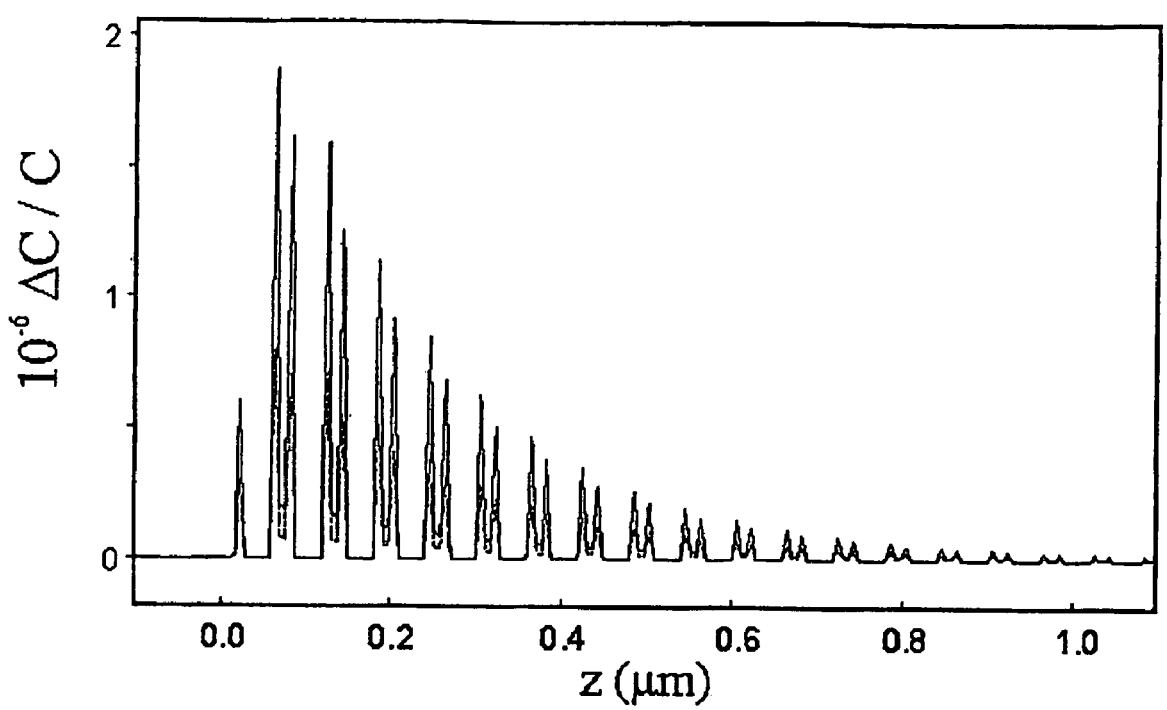
FIG. 4 is a plot depicting fractional collagen denaturation at the onset of vaporization at 3 µm; denaturation due to the FEL superpulse structure (solid) is compared to that due to a 16.2 ns pulse with the same average power (dashed).

Having ruled out photothermal bond breaking on the 10 ns timescale, collagen denaturation is considered. Measurements of the endothermic denaturation of corneal collagen have been accounted for in an approximate fashion with first-order kinetics, $$\frac{1}{C}\frac{dC}{dt} = \frac{RT(t)}{hN_a} e^{(1+\Delta S^*/R)} e^{-E_a/RT(t)} \quad (3)$$

where $E_a$ (106 kJ mol$^{-1}$) is the activation energy and $\Delta S^*$ (39 J mol$^{-1}$ K$^{-1}$) is the activation entropy (Kampmeier et al., (2000) *Cornea* 19: 355). FIG. 4 plots the fractional collagen denaturation calculated by integration of equation 3 up to the time of explosive vaporization.

While this analytical treatment is applicable until the onset of explosive vaporization, it is possible to comment on later times. The fractional denaturation will continue to increase up to the onset of material removal, which has been observed on the 100 ns timescale (Tribble et al., (1997) *Phys Rev. E* 55: 7385). In addition, during explosive vaporization the energy stored in the superheated liquid is rapidly converted to latent heat, vaporizing ~40% of the saline (Skripov et al., (1988) *Thermophysical Properties of Liquids in the Metastable (Superheated) State*, Gordon and Breach Science Publishers, New York). The temperature of the saline layer falls towards 100° C., where the temperature is a function of pressure. Furthermore, during vapor expansion the pressure in the saline layers and the stress in the protein layers increase until the outer protein layer(s) mechanically fail. Thermomechanical measurements indicate that collagen is ductile in the laminar regions of cornea, with an ultimate tensile strength of approximately 12 MPa, but when thermally denatured, the protein exhibits brittle fracture at ultimate tensile strengths around 1 MPa (Spörl et al., (1997) *Ger. J. Opthamol.* 5: 322). At 3 μm the ductile collagen strains when stressed by the expanding vapor and consequently stores stress energy. Stress increases and propagates until tensile failure, when the stress energy is released and contributes to collateral damage.

This analytical approach allows the investigation of the influence of the Mark III superpulse structure, viewed as a train of picosecond pulses with a repetition rate of 2.85 GHz. In particular, a 16.2 ns pulse with the same average power as the superpulse exhibits similar thermal responses. However, as shown in FIG. 2, the longer pulse duration replaces the staircase and sawtooth with temperature ramps. FIG. 4 indicates that the staircase associated with Mark III irradiation leads to the greater accumulation of denatured collagen, i.e. picosecond pulses are not essential for this application. Instead, the effect is related to the separation in the layer temperatures as shown in FIG. 2, driven by the competition between the layer-specific heating rates and thermal diffusion.

Conclusions from Laboratory Experiment 1

Thermal diffusion in a laminar system representative or cornea was studied, which was heated by a Mark III FEL at rates that satisfy the criterion for superheating of saline. At these temperatures and pulse durations, the model predicts no direct photothermal breaking of chemical bonds.

Figure 5A:
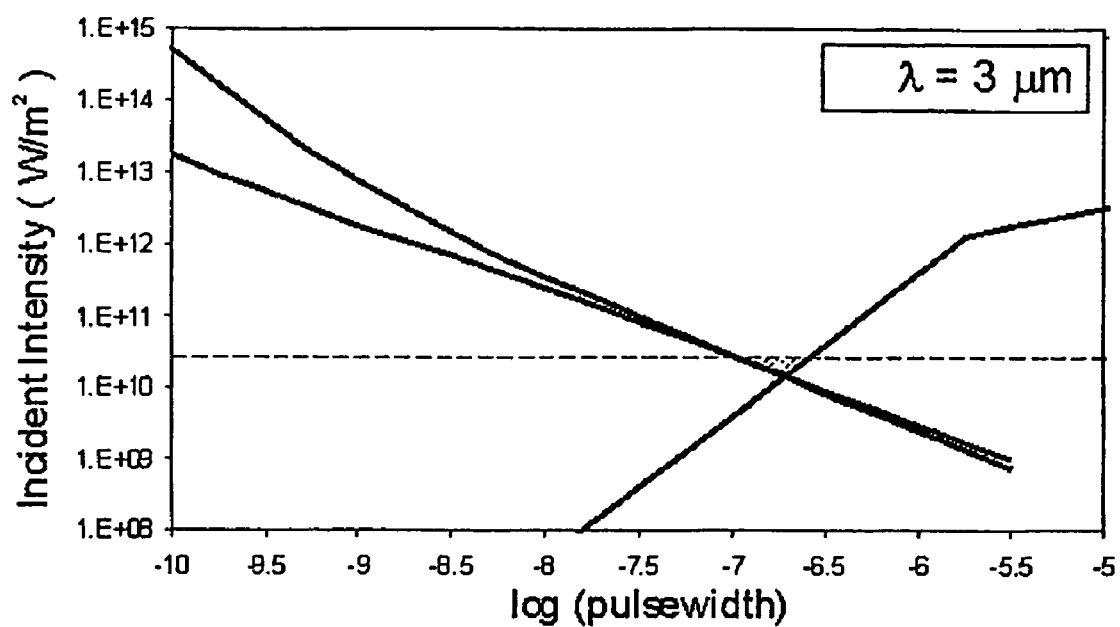
FIG. 5A is a plot of incident intensity as a function of pulse duration for a laser wavelength of 3.00 microns. The hatched region indicates those intensities and pulse durations that satisfy the criteria for a single pulse ablating tissue. The pulse can have a substructure.
Figure 5B:
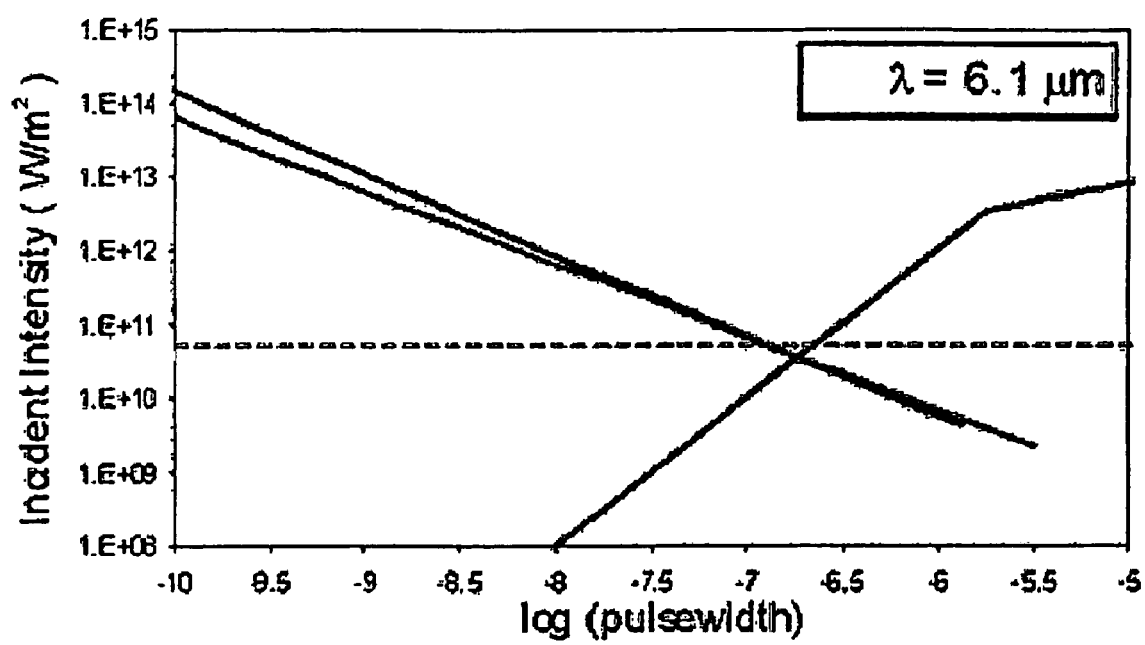
FIG. 5B is a plot of incident intensity as a function of pulse duration for a laser wavelength of 6.10 microns. The hatched region indicates those intensities and pulse durations that satisfy the criteria for a single pulse ablating tissue. The pulse can have a substructure.
Figure 5C:
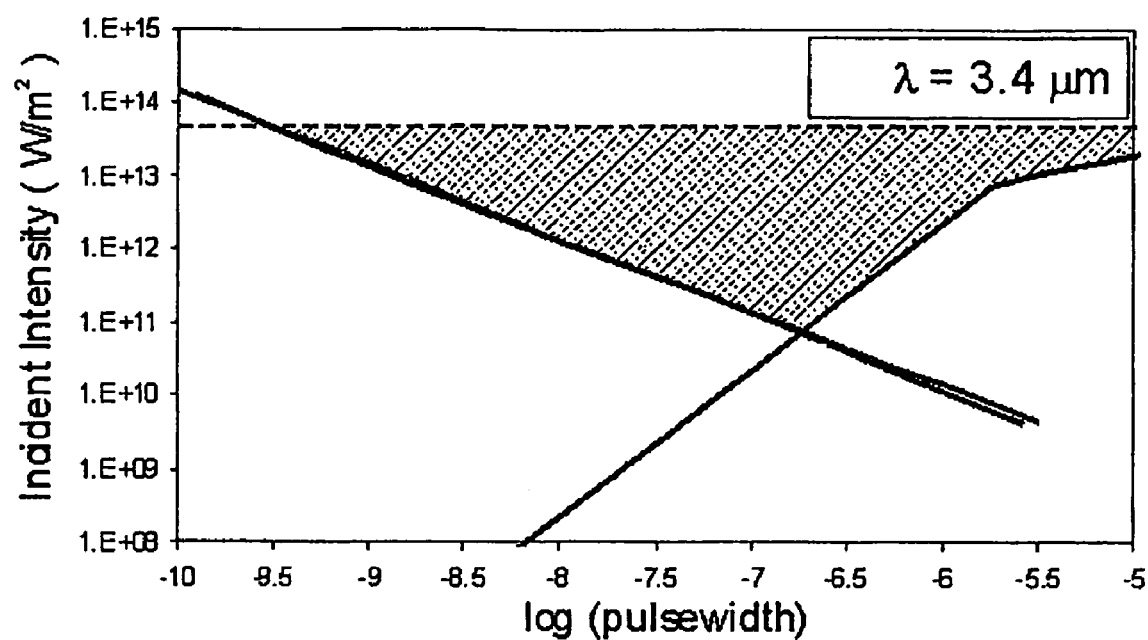
FIG. 5C is a plot of incident intensity as a function of pulse duration for a laser wavelength of 3.40 microns. The hatched region indicates those intensities and pulse durations that satisfy the criteria for a single pulse ablating tissue. The pulse can have a substructure.

FIGS. 5A-5C disclose a range of intensities and pulse durations that meet the criteria for a single pulse to ablate tissue at three infrared wavelengths: FIG. 5A depicts conditions for a wavelength of 3.00 μm; FIG. 5B depicts conditions for a wavelength of 6.10 μm; and FIG. 5C depicts conditions for a wavelength of 3.40 μm. The criteria for thermal denaturation of protein, superheating saline to the critical temperature, and the heterogeneous nucleating density associated with superheating yield the sloped traces. The horizontal line represents the criterion for protein denaturation to precede vaporization. While the pulse duration nominally represents a single pulse, a pulse substructure is allowable. The wavelength 3.40 μm has a relatively large region of intensities and pulse durations that satisfy the criteria, while 3.00 μm and 6.10 μm have relatively small regions. Furthermore, in order to achieve a net ablation rate to render the source a practical device for surgical applications, the average power of a laser employed for that purpose preferably exceeds 100 mW, and is more preferably about 1 W.

REFERENCES

The references listed below as well as all references cited in the specification are incorporated herein by reference to the extent that they supplement, explain, provide a background for or teach methodology, techniques and/or compositions employed herein.

Cole & McGahan, (1993) *J. Heat Transfer* 115: 767

Copeland et al., (2000) International Biomedical Symposium SPIE, San Jose, Calif.

Crook, (1948) *J. Opt. Soc. Am.* 38: 954

Davson, (1972) *The Physiology of the Eye*, Academic Press, New York;

Kampmeier et al., (2000) *Cornea* 19: 355

Edwards et al., (1994) *Nature* 371: 416

Edwards et al., (2002) SPIE 4633:194

Edwards, (1995) *Opt. Eng.* 34(5): 1524

Frank-Kamenetskii, (1969) *Diffusion and Heat Transfer in Chemical Kinetics*, 2$^{nd}$ ed., Plenum Press, New York, Chapters VI and VII Hector et al., (1992) *Int. J. Eng. Sci.* 30: 1731

Joos et al., *Lasers Surg. Med.* (2000) 27: 191

Kampmeier et al., (2000) *Cornea* 19: 355

Landau & Lifshitz, (1987) *Fluid Mechanics*, 2$^{nd}$ ed., Pergamon Press, Oxford, Chapter V Liebman et al., (2000) *The Amide Linkage*, John Wiley and Sons, New York, Chapter V Lim & Shamos, (1974) *Biopolymers* 13:1791

Madey, (1971) *J. Appl. Phys.* 42:1906

Privalov & Tiktopulo, (1970) *Biopolymers* 9: 127

Skripov et al., (1988) *Thermophysical Properties of Liquids in the Metastable (Superheated) State*, Gordon and Breach Science Publishers, New York Spörl et al., (1997) *Ger. J. Opthamol.* 5: 322

Stryer, (1995) *Biochemistry*, 4$^{th}$ ed., W.H. Freeman and Company, New York, p 32

Tribble et al., (1997) *Phys. Rev. E* 55: 7385 van Gemert & Welch, (1995) *Optical-Thermal Response of Laser-Irradiated Tissue*, Plenum Press, New York Venugopalan & Mikić, (1996) *Biophys. J.* 70: 2981

U.S. Pat. No. 5,423,803

U.S. Pat. No. 5,795,351

U.S. Pat. No. 6,086,580

It will be understood that various details of the invention can be changed without departing from the scope of the invention. Furthermore, the foregoing description is for the purpose of illustration only, and not for the purpose of limitation—the invention being defined by the claims.

What is claimed is:

1. A method of ablating a material, the method comprising:
   (a) directing laser radiation at a target material to be ablated, the target material comprising a protein portion and a liquid portion; and
   (b) irradiating the target material with:
      i) one or more pulses of laser radiation having a duration ranging from about 1 nanosecond to about 10 microseconds;
      ii) an energy per pulse greater than about 45 microjoules, and
      iii) an average power greater than about 100 mW;
   wherein the duration, energy per pulse, and average power are selected to produce an incident intensity that is less than a threshold amount such that initiating denaturation of the protein portion of the target material occurs before onset of vaporization of the liquid portion of the target material.

2. The method of claim 1, wherein the target material is a heterogenous material.

3. The method of claim 2, wherein the heterogenous material is tissue.

4. The method of claim 3, wherein the tissue is one of human and animal tissue.

5. The method of claim 1, wherein the laser radiation is emitted by a FEL.

6. The method of claim 1, wherein the laser radiation is emitted by a table top laser.

7. The method of claim 1, wherein the laser radiation is infrared laser radiation.

8. The method of claim 1, wherein the average power is greater than about 1 W.

9. The method of claim 1, wherein the one or more pulses comprise two or more micropulses having a duration of between about 1 picosecond and about 1 nanosecond.

10. The method of claim 1, wherein the one or more pulses are of a predetermined wavelength.

\* \* \* \* \*